(12) United States Patent
Ablordeppey et al.

(10) Patent No.: US 7,700,587 B2
(45) Date of Patent: Apr. 20, 2010

(54) HALOPERIDOL ANALOGS

(75) Inventors: Seth Y. Ablordeppey, Tallahassee, FL (US); Donald M. N. Sikazwe, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 372 days.

(21) Appl. No.: 10/934,769

(22) Filed: Sep. 7, 2004

(65) Prior Publication Data

US 2006/0052363 A1   Mar. 9, 2006

(51) Int. Cl.
| | |
|---|---|
| A61P 25/18 | (2006.01) |
| A61K 31/55 | (2006.01) |
| A61K 31/445 | (2006.01) |
| A61K 31/40 | (2006.01) |
| C07D 207/00 | (2006.01) |
| C07D 207/46 | (2006.01) |
| C07D 211/00 | (2006.01) |
| C07D 211/20 | (2006.01) |
| C07D 225/04 | (2006.01) |
| C07D 243/08 | (2006.01) |
| C07D 295/00 | (2006.01) |
| C07D 487/00 | (2006.01) |

(52) U.S. Cl. .............. 514/218; 514/317; 514/327; 514/412; 514/424; 514/428; 540/461; 540/575; 546/217; 546/237; 548/556; 548/571

(58) Field of Classification Search .......... 514/218, 514/317, 327, 412, 424, 428; 540/461, 575; 546/217, 237; 548/556, 571
See application file for complete search history.

(56) References Cited

U.S. PATENT DOCUMENTS

| 3,334,826 A | 8/1967 | McLean ............ 242/436 |
| 3,438,991 A | 4/1969 | Janssen ............ 260/294.7 |
| 3,539,573 A | 11/1970 | Schmutz et al. ...... 260/268 |
| 5,229,382 A | 7/1993 | Chakrabarti et al. ... 514/220 |

OTHER PUBLICATIONS

Ablordeppey et al., Design and Synthesis of Novel Analogs of Haloperidol Incapable of Forming MPP+-Like Species, Medicinal Chemistry Research, (7), pp. 459-467, 1993.*

Lyles-Eggleston et al., Design, Synthesis, and Evaluation of Metabolism-Based Analogues of Haloperidol Incapable of Forming MPP+-like Species, Journal of Medicinal Chemistry, Jan. 29, 2004, vol. 47, No. 3, pp. 497-508, especially p. 498—relevant to claims 1-5.

Creese et al., Science 192:481-483, 1976.
Rowley, M., et al., *J. Med. Chem.*, 2001, 44(4), 477.
Jaber, M., et al., *Neuropharm.*, 1996, 35(11), 1503.
Eyles, D., et al., *Life Sci.*, 1997, 60, 529.
Boulay, D., et al., *Eur. J. Pharmacol.*, 2000, 391, 63.
Missale, C., et al., *Physiol. Rev.*, 1998, 78, 189.
Sikazwe, et al., *Bioorganic & Medicinal Chemistry Letters*, 13, 2003, 3779-3782.
Schmidt et al., *Eur. J. Pharmacol.*, 2001, 425, 197.
Needham et al., *Psychopharmacol Bull.*, 1996, 32(1), 123.

* cited by examiner

*Primary Examiner*—Brenda L Coleman
(74) *Attorney, Agent, or Firm*—Dennis P. Clarke

(57) ABSTRACT

Haloperidol analogs that conforms to the structural formulae:

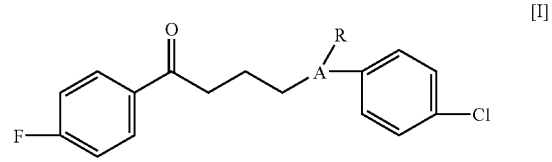

[I]

wherein: R is H, or —(CH$_2$)$_n$—OH,
n is an integer from 0 to 2, and
A is a heterocyclic bridging group, consisting essentially of carbon and at least one nitrogen atom, which effectively maintains the distance between the moieties connected thereby such that the compound (1) is incapable of metabolizing to BCPP$^+$ like species, (2) has an affinity for the D2 receptor subtype of 15<D2<250 and (3) functions as a dopamine receptor antagonist, or the structural formulae:

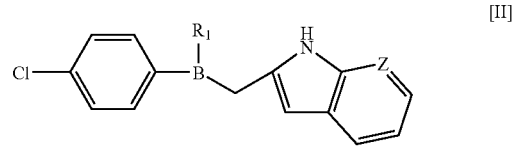

[II]

wherein: R$_1$ is H, or —(CH$_2$)$_n$—OH,
n is an integer from 0 to 2,
B is an aza- or diaza-bicyclo group, which effectively maintains the distance between the moieties connected thereby such that the compound is incapable of metabolizing to BCPP$^+$ like species; and
Z is —CH— or N; and pharmaceutically acceptable salts, esters, derivatives, metal complexes, conjugates and prodrugs thereof.

3 Claims, 2 Drawing Sheets

Apomorphine climbing data:
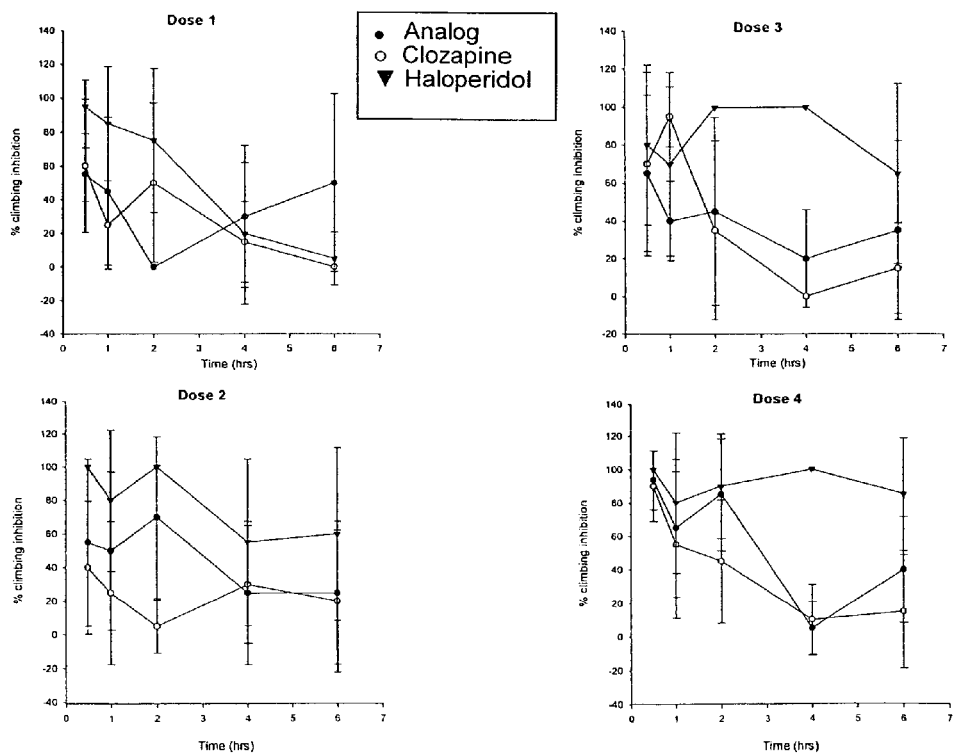
Figure 1. % inhibition of apomorphine induced climbing behavior at selected time points. Data reporte as mean % ± SEM, n=2.

Catalepsy data:
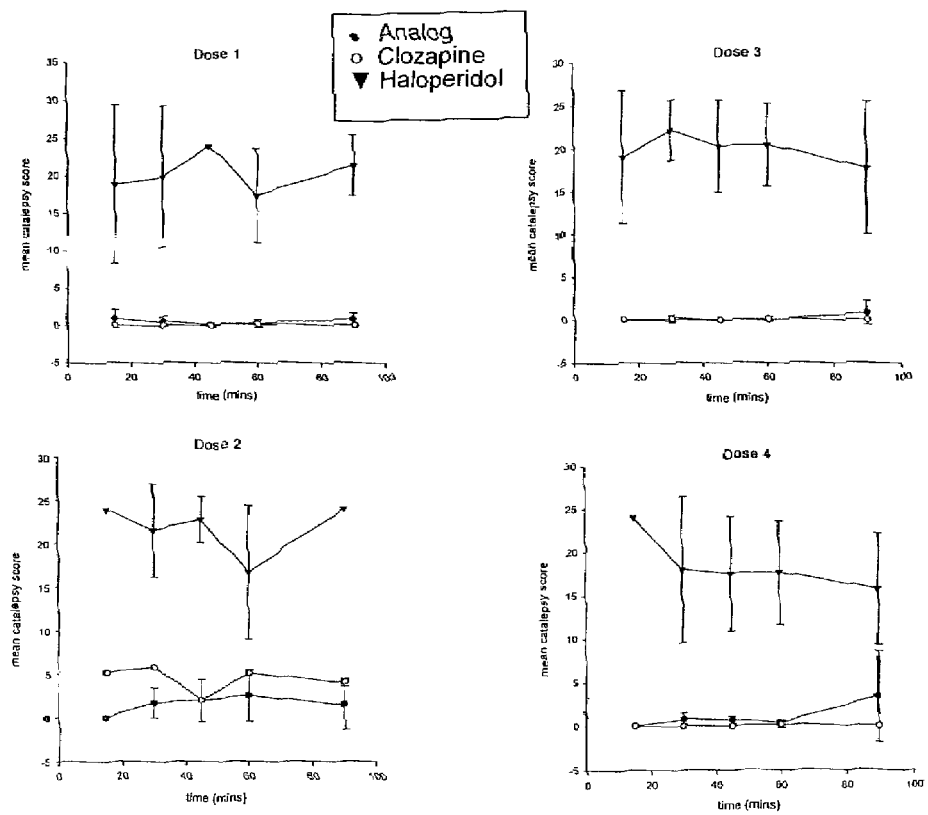
Figure 2. The Plots represent mean catalepsy scores recorded at different time points over a 90 m period. Data reported as mean catalepsy score ± SEM, n=3.

HALOPERIDOL ANALOGS

This study was supported by NIGMS MBRS # GM 08111, RCMI G12 RR 03020, and Title III grants. The United States Government has certain rights to the invention described herein.

BACKGROUND OF THE INVENTION

1. Field of the Invention

The present invention relates to analogs of haloperidol possessing anti-psychotic properties and clozapine-like therapeutic profiles.

2. Description of the Prior Art

Schizophrenia is a chronic disease that is characterized by positive (hallucinations, delusions), negative (social withdrawal, flattened affect) and cognitive (formal thought disorder, executive memory dysfunction) symptoms. The dopamine hypothesis, that schizophrenia stems from excessive midbrain dopamine transmission, originated from studies with neuroleptics that revealed correlations between clinical efficacy, effects on dopamine metabolism (Carlsson & Lindqvist, Acta Pharmacol. Toxicol. 20:140-144, 1967) and binding to dopamine receptors (Creese et al., Science 192: 481-482, 1976). In addition, drugs that increase synaptic dopamine concentration, (e.g., amphetamines) produce aberrant, stereotyped behavior in animals (W T McKinney, in S C Shultz and C A Tamminga (eds) Schizophrenia: Scientific Progress. Oxford University Press, New York, pp 141-154, 1989) and schizophrenia-like symptoms in humans (Snyder, Am. J. Psychol. 130:61-67, 1976).

The therapeutic treatment of schizophrenic patients, as well as patients suffering from other psychoses, by the administration of neuroleptic drugs. One class of such drugs comprises the so-called typical antipsychotic agents (TAAs), such as chlorpromazine [2-chloro-N,N-dimethyl-10H-phenothiazine-10-propanamine, described in U.S. Pat. No. 2,645,640], haloperidol [4-[4-(4-chlorophenyl)-4-hydroxy-1-piperidinyl]-1-(4-fluorophenyl)-1-butanone, described in U.S. Pat. No. 3,438,991], sulpiride [5-aminosulfonyl)-N-[(1-ethyl-2-pyrrolidinyl)methyl]-2-methoxybenzamide, described in U.S. Pat. No. 3,334,826], and chemically closely related compounds, is widespread. Haloperidol is a drug of choice in the treatment of schizophrenia and acts in part by inhibiting dopamine receptors in the CNS [Seeman, P.; Lee, T.; Chau-Wong, M.; Wong, K *Nature*, (1976), 261, 717]. While control of schizophrenic symptoms has been successful, treatment with these drugs does not cure the psychotic patient, who will almost certainly relapse if medication is discontinued.

Moreover, some of the known neuroleptics produce unwanted side effects. For example, the side effects of many antipsychotic drugs such as haloperidol, for example, include the so-called extrapyramidal symptoms (EPS), such as rigidity and tremor, continuous restless walking, akathisia, dystonia, late dyskinesia and tardive dyskinesia (TD), e.g., Parkinsonism dyskinesia, which causes facial grimacing, and involuntary movements of the face and extremities. The occurrence of orthostatic hypotension in patients taking antipsychotic drugs is also common. These side effects are believed to be caused by blockage of the dopaminergic neurotransmission by the administered neuroleptics [Rowley, M.; Bristow, L. J.; Hutson, P. H. *J Med. Chem.* 2001, 44 (4), 477; Jaber, M.; Robinson, S. W.; Missale, C.; Caron, M. G. *Neuropharm.* 1996, 35 (11), 1503; Capuano, B.; Crosby, I. T.; Lloyd, E. J. *Curr. Med. Chem.* 2002, 9, 521.

The incidence rate of TD increases throughout the patient's exposure to antipsychotic drugs. The longer the exposure, the higher the patient's risk of developing, e.g., TD. This phenomenon points to the inadequacy of preclinical trials which only assess the risk of TD during the trial period. This phenomenon also suggests that the neuronal insults associated with TD are cumulative and the process which leads to this disease may be insidious and subtle in nature.

Anticholinergic agents such as Cogentin.RTM., have been used to reduce the Parkinson-like side effects, but these also cause their own side effects such as mental and/or physical impairment, tachycardia, dysuria and gastrointestinal symptoms.

Recently, atypical antipsychotic agents (AAAs), such as clozapine [8-chloro-1-(4-methyl-1-piperazinyl)-5H-dibenzo[b,e]-[1,4]-diazepine, described in U.S. Pat. No. 3,539,573] and olanzapine [2-Methyl-10-(4-methyl-1-piperazinyl)-4H-thieno-[2,3-b][1,5]benzodiazepine, described in U.S. Pat. No. 5,229,382], have been introduced, which possess a therapeutic profile exhibiting greatly reduced Parkinson-like side effects. However, the TAAs also possess unwanted side effects as well, e.g., hypotension, sedation, confusion, weight gain, inter alia. Therefore, large numbers of patients continue to receive the TAAs such as, e.g., haloperidol.

Thus, there exists a continuing need in the art for antipsychotic drugs for the treatment of psychoses that produce fewer or less severe manifestations of the above discussed common side effects. In addition, because of the frequent long term administration of neuroleptics and the problems with patient compliance, there is a further need in the art for long lasting neuroleptics, which can be formulated into sustained release depot preparations, without causing the side effects mentioned above.

SUMMARY OF THE INVENTION

The above and other needs of the art are realized by the present invention, one embodiment of which relates to haloperidol analogs that conform to the structural formulae:

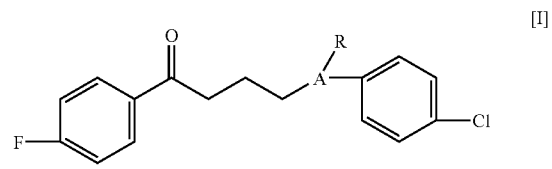

[I]

wherein: R is H, or —$(CH_2)_n$—OH, n is an integer from 0 to 2, and

A is a heterocyclic bridging group, consisting essentially of carbon and at least one nitrogen atom, which effectively maintains the distance between the moieties connected thereby such that the compound (1) is incapable of metabolizing to $BCPP^+$ like species, (2) has an affinity for the D2 receptor subtype of 15<D2<250 and (3) functions as a dopamine receptor antagonist; and pharmaceutically acceptable salts, esters, derivatives, metal complexes, conjugates and prodrugs thereof.

A further embodiment of the invention concerns haloperidol analogs that conform to the structural formulae:

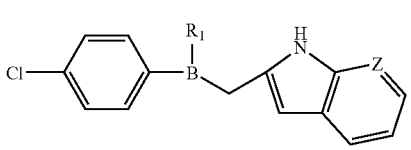

[II]

wherein: $R_1$ is H, or —$(CH_2)_n$—OH,
n is an integer from 0 to 2,

B is an aza- or diaza-bicyclo group, which effectively maintains the distance between the moieties connected thereby such that the compound is incapable of metabolizing to BCPP⁺like species; and Z is —CH— or N; and pharmaceutically acceptable salts, esters, derivatives, metal complexes, conjugates and prodrugs thereof.

A further embodiment of the invention concerns a method for treating a patient suffering from psychosis comprising administration to the patient of a therapeutically effective amount of a haloperidol analog having one of the above structures.

Another embodiment of the invention comprises a pharmaceutical composition comprising a haloperidol analog having one of the above structures and a pharmaceutically acceptable carrier.

A still further embodiment of the invention relates to an article of manufacture comprising packaging material and a pharmaceutical agent contained within the packaging material, wherein the pharmaceutical agent is effective for the treatment of a subject suffering from psychosis, and wherein the packaging material comprises a label which indicates that the pharmaceutical agent can be used for ameliorating the symptoms associated with psychosis, and wherein the pharmaceutical agent is a haloperidol analog having one of the above structures.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 1 and 2 are graphs plotting the pharmaceutical profiles of the compounds of the invention.

DETAILED DESCRIPTION OF THE INVENTION

The mechanism by which haloperidol induces extrapyramidal symptoms (EPS) is still a subject of ongoing research. It has been shown that haloperidol is oxidatively biotransformed to a neurotoxic metabolite BCPP⁺ (HPP⁺) according to the equation:

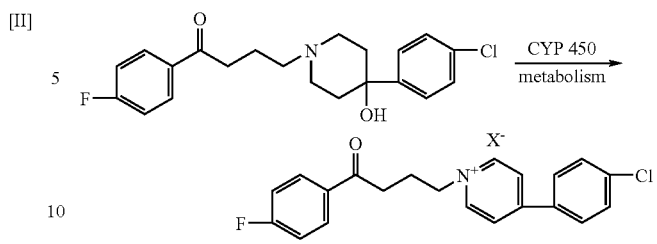

and that BCPP⁺ destroys dopamine neurons [Eyles, D. W.; Avent, K. M.; Stedman, T. J.; Pond, S. M. *Life Sci.* 1997, 60, 529; Subramanyam, B.; Rollema, H.; Woolf, T.; Castagnoli, N., Jr. *Biochem. Biophys. Res. Commun.* 1990, 166, 238;].

Persistent reports, however, point to high D2 binding by haloperidol in the brain's nigrostriatal areas as the cause for acute EPS [Boulay, D.; Depoortere, R.; Oblin, A.; Sanger, D. J.; Schoemaker, H.; Perrault, G. *Eur. J. Pharmacol.* 2000, 391, 63; Tarsy, D. *Clin. Neuropharmacol.* 1983, 6, S9; Missale, C.; Nash, S. R.; Robison, S. W.; Jaber, M.; Caron, M. G. *Physiol. Rev.* 1998, 78, 189; Sikazwe, et al, *Bioorganic & Medicinal Chemistry Letters*, 13 (2003), 3779-3782. These observations are consistent with the occupancy theory of Crocker et al, [*Neuro-Psychophamacol. Biol, Psychiatry*, 2001, 25, 573-590] which indicates that induction of catalepsy is associated with high D2 occupancy.

The present invention is predicated on the discovery of certain analogs of haloperidol that do not form quaternary pyridinium metabolites, that have decreased D2 binding affinity and also possess antidopaminergic, i.e., antipsychotic properties. The compounds of the invention may be characterized as analogs of haloperidol with clozapine-like therapeutic profiles.

The preferred analogs conform to the structural formulae:

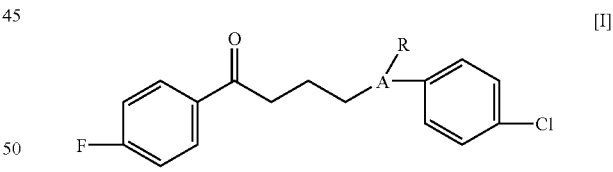

[I]

wherein: R is H, or—$(CH_2)_n$—OH,
n is an integer from 0 to 2, and

A is a heterocyclic bridging group, consisting essentially of carbon and at least one nitrogen atom, which effectively maintains the distance between the moieties connected thereby such that said compound (1) is incapable of metabolizing to BCPP⁺ like species, (2) has an affinity for the D2 receptor subtype of 15<D2<250 and (3) functions as a dopamine receptor antagonist; and pharmaceutically acceptable salts, esters, derivatives, metal complexes, conjugates and prodrugs thereof.

One preferred analog is that having the formula:

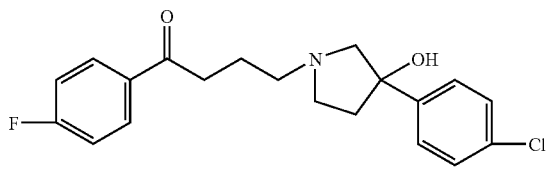

[A]

The racemic mixture of the above compound, as well as the other compounds of the invention exhibit much less severe EPS (manifested as catalepsy in animal models) than haloperidol, do not form quaternary pyridinium metabolites, have decreased D2 binding affinity and act as antidopaminergics in vivo, as shown using the apomorphine induced climbing behavioral test.

While not wishing to be bound by any theory as to the mechanism of the invention, it is hypothesized that while acute EPS is related to potent D2 occupancy, BCPP+ may contribute to some of the long term side effects such as TD. The above analog [A] exhibits low (Ki=33 nM) D2 binding affinities, has a KiD2/KiD4 ratio >1 and is incapable of forming BCPP+-like metabolites. Analog [A] and its (+) enantiomer were tested for cataleptogenic effects in male Sprague Dawley (SD) rats using the conventional "bar test". Catalepsy induction in animals is recognized as an indicator for EPS in humans. Haloperidol (a cataleptogenic agent) and Clozapine (a non cataleptogenic agent) were used as positive controls in the tests described below.

Analog [A] was designed by replacing haloperidol's piperidine with a pyrrolidine ring so that it could not be metabolized to BCPP+-like species. The advantage of using this ring is that it cannot be biotransformed to quarternary pyridinium species [Missale, C.; Nash, S. R.; Robison, S. W.; Jaber, M.; Caron, M. G. *Physiol. Rev.* 1998, 78, 189]. Dehydration can occur in this ring but oxidation leads to pyrrole formation in lieu of the quarternary species. This design, therefore, ruled out pyridinium species participation leaving only D2 affinity as the primary contributor to EPS. Analog [A]-[4-[3-hydroxy-3-(4'chlorophenyl)pyrrolidinyl]-4"-flourobutyrophenone] may be synthesized according to the method reported by Ablordeppey et al, [Ablordeppey, S. Y.; Borne, R. F. *Med. Chem. Res,* 1993, 3, 459-467].

Haloperidol (1), Analog [A] (2), and clozapine (3) were evaluated in vitro for human D2 like (D2, D3 & D4) receptor binding affinities by measuring their ability to displace standard competitive radioligands according to the method of Schmidt et al [*Eur. J. Pharmacol,* 2001, 425, 197]. The data is summarized in table 1.

TABLE 1

In Vitro binding affinities (Ki (nM) and pKi 4: SEM (n)) for cloned human DA receptors (D2, D3, and D4) by reference compounds and 2. All compounds had satisfactory analytical data.

| Compounds | Ki D2 pKi | Ki D3 pKi | Ki D4 pKi |
|---|---|---|---|
| Haloperidol (1) | 0.89 | 4.6 | 10 |
|  | 9.05 ± 0.30 (3) | 8.34 ± 0.27 (3) | 7.98 ± 0.28 (3) |
| Analog [A] (2) | 33 | 200 | 11 |
|  | 7.48 ± 0.18 (3) | 6.7 ± 0.014 (3) | 7.93 ± 0.07 (3) |

TABLE 1-continued

In Vitro binding affinities (Ki (nM) and pKi 4: SEM (n)) for cloned human DA receptors (D2, D3, and D4) by reference compounds and 2. All compounds had satisfactory analytical data.

| Compounds | Ki D2 pKi | Ki D3 pKi | Ki D4 pKi |
|---|---|---|---|
| (+) Analog [A] | 51.1 ± 6.0 | 1069± | 3.6 ± 0.48 |
| Clozapine (3)[a] | 130 | 240 | 54 |
|  | 6.87 0.10 (3) | 6.62 0.05 (10) | 7.27 ± 0.06(36) |

[a]see Schmidt et al, *Eur. J Pharmacol,* 2001, 425, 197].

From Table 1 it can be seen that the Ki D2/D4 ratios for the tested compounds are Haloperidol - 0.1; Clozapine - 2.4 and analog [A] - 3 and (+)Analog [A] - 14.2.

Apomorphine induced climbing-stereotypy: A modified climbing test by Needham et al [*Psychopharmacol Bull.* 1996, 32(1), 123] was used. 13 Swiss male mice (20-25 gm, N=125) in groups of 5 per time point (30 min, 1 hr, 2, 4, & 6 hrs) were injected intraperitonealy with 0.1 ml/kg of vehicle (0.1% lactic acid and 0.9% saline) or increasing moles/kg equivalent doses of dopamine antagonists 1, 2 (i.e., $5.3\times10^{-7}$; $1.9\times10^{-6}$; $3.2\times10^{-6}$; $5.3\times10^{-}$), and 3 ($3.1\times10^{-5}$; $9.2\times10^{-5}$; $1.5\times10^{-4}$; $2.4\times10^{-4}$). Animals were then challenged with $2.8\times10^{-6}$ moles/kg of the agonist (apomorphine), placed in cylindrical wire cages (12 cm in diameter, 14 cm in height), and observed for climbing behavior at 10 and 20 minutes post dose. Climbing behavior was assessed as follows: 4 paws on the cage floor=0 score; 2 and 3 paws on the cage=I score; 4 paws on the cage=2 scores. Scores were expressed as mean % climbing inhibition, and plotted in FIG. 1.

Bar test for catalepsy: A modified bar test by Needham et al, supra was used. 13 Male SD rats (200-300 gm, N=100) were injected subcutaneously with 1 ml/kg of vehicle (<0.005% acetic acid in $H_2O$) or increasing moles/kg equivalent doses of 1, 2 (i.e., $5.3\times10^{-7}$; $1.9\times10^{-6}$; $3.2\times10^{-6}$; $5.3\times10^{-6}$), and 3 ($3.1\times10^{-1}$; $9.2\times10^{-5}$; $1.5\times10^{-4}$; $2.4\times10^{-4}$). Catalepsy severity was assessed immediately at various time points (15, 30, 45, 60, and 90 min) post injection, by scoring how long the rat maintained both forepaws motionless on a horizontal metal bar (1.1 cm in diameter, 10 cm above the bench top in a box). A score of 1 was given for every 5 seconds (2 min. maximum) the animal remained on the bar. Mean scores from 5 animals per time point were recorded for catalepsy and plotted in FIG. 2.

Statistical analysis: The student t-test was used to compare the three compounds used in the animal behavioral tests. Results were considered significant at $p<0.05$.

Table 1 lists binding affinities of the analog and the controls at D2-like receptors. Affinities were determined by competitive radioligand displacement assays. In order to assess their EPS potential (expressed as catalepsy), the D2 subtype affinities of the analog were studied since this appears to be associated with catalepsy [Boulay, D.; Depoortere, R.; Oblin, A.; Sanger, D. J.; Schoemaker, H.; Perrault, G. *Eur. J Pharmacol,* 2000, 391, 63]. Statistical analysis of both behavioral test data, revealed that the analog's effects were significantly different from compound 1 but non significantly different from compound 3 at all four doses (FIGS. 1 and 2).

From the foregoing, compounds 1, 2 and 3 exhibited different binding affinities (Ki=0.89, 33, and 130 nM) for the D2 subtype, respectively. The analog (2) showed a decreased (37 fold lower) binding affinity for D2 compared to haloperidol. Also, (2) was determined to possess approximately four fold higher affinity for the same receptor (D2) than 3. Since 2 could inhibit apormophine induced climbing in mice, it meant that (like 1 and 3) this compound was acting as a dopamine receptor antagonist. Most importantly, 2 exhibited no catalepsy in rats at the doses used. The catalepsy profile of (2) was statistically similar to clozapine's. Since compound (2) cannot form quaternary pyridinium species (BCPP$^+$), its lack of cataleptogenicity can therefore be attributed to its decreased D2 binding affinity. This data suggests that haloperidol's high D2 binding may play a more central role in acute EPS.

Administration of the analogs of the invention may be accomplished either therapeutically or prophylactically by means of pharmaceutical compositions which are prepared by techniques well known in the pharmaceutical sciences. While the compounds of the invention are preferably administered orally or intrarectally, they may also be administered by a variety of other routes such as transdermally, subcutaneously, intranasally, intramuscularly and intravenously.

The present invention is also directed to pharmaceutical compositions which include at least one compound as described above in association with one or more pharmaceutically acceptable diluents, excipients or carriers therefore. In making the pharmaceutical compositions of the present invention, one or more compounds will usually be mixed with, diluted by or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 60% by weight of active compound, soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The dose of the compound is that amount effective to prevent occurrence of the symptoms of the disease or to treat some symptoms of the disease from which the patient suffers. By "effective amount," "therapeutic amount" or "effective dose" is meant that amount sufficient to elicit the desired pharmacological or therapeutic effects, thus resulting in effective prevention or treatment of the disease. Prevention of the disease is manifested by a prolonging or delaying of the onset of the symptoms of the disease. Treatment of the disease is manifested by a decrease in the symptoms associated with the disease or an amelioration of the recurrence of the symptoms of the disease.

The effective dose may vary, depending upon factors such as the condition of the patient, the severity of the symptoms of the disease and the manner in which the pharmaceutical composition is administered. Generally, the compounds of the invention are administered in essentially the same manner and in dosages conventionally employed in connection with the administration of clozapine.

The compositions are formulated, preferably in a unit dosage form, such that each dosage contains from about 25 to about 900 mg, more usually about 25 to about 150 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more of the above-described suitable pharmaceutical diluents, excipients or carriers.

The compounds are effective over a wide dosage range in treating psychoses. Thus, as used herein, the term "effective amount" refers to a dosage range of from about 25 to about 900 mg of body weight per day. In the treatment of adult humans, the range of about 25 to about 900 mg, in single or divided doses, is preferred. However, it will be understood that the amount of compound actually administered will be determined by a physician in light of the relevant circumstances, including (1) the condition to be treated, (2) the choice of compound to be administered, (3) the chosen route of administration, (4) the age, weight and response of the individual patient, and (5) the severity of the patient's symptoms. Therefore, the above dosage ranges are not intended to limit the scope of the invention in any way.

From the foregoing description, various modifications and changes in the composition and method will occur to those skilled in the art. All such modifications coming within the scope of the appended claims are intended to be included therein. The entire disclosures and contents of each and all references cited and discussed herein are expressly incorporated herein by reference. All percentages expressed herein are by weight unless otherwise indicated.

In the following examples, which set forth methods for preparing the analogs of the invention, melting points were taken on a Thomas-Hoover Unimelt (uncorrected) or determined in open capillaries on Gallenkamp electrothermal apparatus. Infrared spectra were determined on a Perkin-Elmer model 28 1B 1H. Two dimensional homonuclear correlated spectroscopy (COSY), attached proton test (APT), Heteronuclear correlated (HETCOR) and Nuclear Overhauser Effect spectroscopy (NOESY) spectra were used to make specific hydrogen and carbon assignments. Electron-impact (70 eV) mass spectra were taken on a Finnigan 3200 GC/MS using either Digital or Technivent brand data systems. All flash column chromatography incorporated silica gel 60 (230-400 mesh) or (200-425 mesh) and gravity column chromatography was performed on silica gel (70-230 mesh). Gas chromatographic analyses were performed on a Hewlett-Packard GC model 5890A with both NPD and FID detectors and an HP 3394A integrator. Elemental analyses were performed by Atlantic Microlab, Atlanta, Ga. Haloperidol (free base) was obtained from Sigma Chemical company, St. Louis, Mo. Precoated silica gel plates (Analtech 17254, 0.25 mm; Merck) were used for TLC analysis. $^1$H NMR spectra were recorded either on a Varian EM-300 MHz, a Varian VXR 300 (300/75 MHz) spectrometer or on a Bruker AM 270 MHz instrument, with DMSO-d6 or CDC 13 as the solvent; all values are expressed in 6 values (parts per million). The following abbreviations are used: s=singlet, d=doublet, t=triplet, p=pentet, dd=doublet doublet, in =multiplet, and br=broad. Compounds were named using Autonom in Chem Draw version 7.0.1. Elemental analyses (C. H, N) were performed by Atlantic Microlab, Inc.; the analytical results were within +0.4% of the theoretical values for the formula given.

EXAMPLE 1

4-[3-hydroxy-3-(4'-chlorophenyl)pyrrolidinyl]-4"-fluorobutyrophenone [A1] 1-Carbethoxy-3-hydroxy-3-(4'-chlorophenyl)pyrrolidine (1). Grignard reagent for this reaction was obtained from Mg (3.1 g, 0.129 g-atom), 1-bromo-4-chlorobenzene (23.0 g, 0.12 mol.) and anhydrous Et20 (200 mL) and the resulting mixture was refluxed for 5 h. A solution of ketone

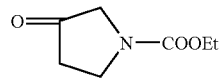

(13.3 g, 0.085 mol.) in dry THF (100 mL) was added rapidly and the resulting mixture was allowed to reflux with stirring for 24 h. The mixture was allowed to cool and 30% $NH_4Cl$ solution was added until all solids dissolved. The aqueous phase was separated and extracted with $Et_2O$ (3×100 mL). The combined organic phase was shaken with $H_2O$ (50 mL) and dried ($Na_2SO_4$). The solvent was removed under reduced pressure to afford an oil (13.7 g, 60%). Column chromatography on silica gel afforded the desired product; mp 83-86° C. IR (Neat, $cm^{-1}$) 3400 (br., OH), 1680 (NCOOEt). $^1$H-NMR ($CDCl_3$) δ 1.20-1.27 (t, 3H, $CH_3$), 2.13-2.27 (m, 2H, C4-H), 3.52-3.76 (m, 4H, C2-H & C5-H), 4.04-4.12 (m, 2H, $OCH_2$), 7.31-7.42 (dd, 4H)

3-Hydroxy-3-(4'-chlorophenyl)pyrrolidine (2). A mixture of 1 (2.5 g, 0.016 mol) in absolute ethanol (70 mL) and 50% aqueous potassium hydroxide (21 mL) was refluxed under N2 for 12 h. The solution was cooled, alcohol was removed in vacuo, and $H_2O$ (100 mL) was added. The resulting mixture was extracted with $CHCl_3$ (3×100 mL). The combined $CHCl_3$ extract was washed with $H_2O$ (50 mL) and dried ($MgSO_4$). The solvent was removed in vacuo to afford a whitish solid (1.55 g, 84.6%); mp 113-115° C. LC/MS 198 (M+1), 180.

4-[3-hydroxy-3-(4'-chlorophenyl)pyrrolidinyl-4"-fluorobutyrophenone [A]. A mixture of 2 (1.5 g, 7.6 mmol.), γ-chloro-p-fluorobutyrophenone (6.0 g, 0.030 mol.), $K_2CO_3$ (3 g) and KI (100 mg) in DME (40 mL) was allowed to reflux for 7 h. The mixture was allowed to cool to room temperature, diluted with $H_2O$ (100 mL), extracted with $Et_2O$ (3×100 mL) and dried ($Na_2SO_4$). The solvent was removed under reduced pressure and the residue was chromatographed over silica gel to afford the desired product. Crystallization from methanol/anhydrous $Et_2O$ afforded light yellowish crystals (2.74 g, 83%); mp 79-80° C. LC/MS, 362 ($M^++H$), 364 {(M+2)+H}. $^1$H-NMR ($CDCl_3$), δ, 1.97 (t, 3H, $CH_3$), 1.92-2.02 (quintet, 2H, C7-$H_2$), 2.07-2.17 (m, 1H, C4-H), 2.21-2.31 (m, 1H, C4-H), 2.44-2.52 (ddd, 1H, C5-H), 2.55-2.58 (d, 1H, C2-H), 2.59-2.66 (m, 2H, C6-H), 2.94-2.97 (d, 1H, C2-H), 3.02 (t, 2H, C8-H), 3.09-3.16 (ddd, 1H, C5-H), 7.13 (t, 2H, C3"-H & C5"-H), 7.27-7.30 (d, 2H, C2'-H & C6'-H), 7.40-7.43 (d, 2H, C3'-H & C5'-H), 7.98-8.02 (dd, 2H, C2"-H & C6"-H).

EXAMPLE 2

The method of Bercz [Bercz, C. V.; Ice, R. D. Synthesis of 1-carbethoxy-4-cyano-4-phenylpiperidine, *J. Pharm. Sci.* 1972. 61, 1316-1317] was employed to obtain the starting material

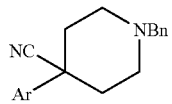

for the synthesis of 5 {4-(4'-Chlorophenyl)-4-methylenehydroxy-1-[4-(4-fluorophenyl)$_4$-oxobutyl]piperidine}.

Hydrolysis of 21 to form acid 22 [4-(4'-Chlorophenyl)-4-carboxy-1-phenylpiperidine], followed by esterification and reduction of the ester yielded intermediate 23

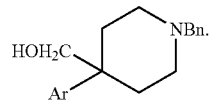

Debenzylation of 23 and sub-sequent alkylation produced compound 5.

4-(4'-Chlorophenyl)-4-carboxy-1-phenylpiperidine (22). A mixture of H2O (1 mL) and sulfuric acid (2 mL) was added to compound 21 (2 g), and the resulting mixture was refluxed overnight. Solvent was removed under vacuum to produce a residue. The residue was dissolved in MeOH (20 mL), and concentrated sulfuric acid (3 mL) was added. The resulting mixture was stirred under reflux overnight, cooled to room temperature, neutralized with $Na_2CO_3$, and extracted with EtOAc (3×30 mL). The pooled organic solution was washed with saturated $Na_2CO_3$ and brine, dried over sodium $Na_2SO_4$, and concentrated in vacuo. The residue was chromatographed over silica gel with hexane/EtOAc (2/1) to give 22 (1.04 g). $^1$H NMR (300 MHz, $CDCl_3$): δ 7.23 (m, 9H), 3.65 (m 3H), 3.45 (s, 2H), 2.78 (d, 2H), 2.50 (d, 2H), 2.15 (t, 2H), 1.92 (t, 2H).

4-(4'-Chlorophenyl)-4-methylenehydroxy-1-[4-(4-fluorophenyl)-4-oxobutyl]piperidine Hydrogen Oxalate (5). To a solution of 22 (0.22 g, 0.67 mmol) in THF (4 mL) was added Superhydride (1.5 mL) and the resulting mixture was stirred at room temperature for 1 h. The reaction was quenched with saturated $Na_2CO_3$ and extracted with EtOAc (3×100 mL). The combined extracts were washed with brine, dried over $Na_2SO_4$, and concentrated in vacuo to give crude product 23. To a solution of the above crude product 23 (202 mg, 0.64 mmol) in $CH_2Cl_2$ (5 mL) was added 2-chloroethyl chloroformate (0.14 mL), and the resulting mixture was stirred at 60° C. for 2 h. The solvent was removed and MeOH (4 mL) was added. After the mixture was refluxed for 3 h, it was cooled to room temperature, solvent was removed, and the residue was converted to the HCl salt 24

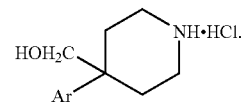

A mixture of 24 (0.34 g, 1.3 mmol), $K_2CO_3$ (0.6 g), KI (0.1 g), and 14 (0.51 g, 2.5 mmol) in DME (10 mL) was stirred at 90° C. overnight and then cooled to room temperature. EtOAc (30 mL) was added, and the mixture was washed with brine, dried over $Na_2SO_4$, concentrated in vacuo, and chromatographed over silica gel to give the desired crude product (0.14 g, 23%), which was subsequently converted to the oxalate salt 5. The resulting colorless, soft solid could not crystallize and was thus submitted for analysis and testing as such. $^1$H NMR (300 MHz, CDCl3): δ 8.01 (dd, J=5.4, 3.4 Hz, 2H), 7.32 (m, 4H) 7.13 (t, J=8.8 Hz, 2H), 3.56 (s, 2H), 2.96 (t, J=6.8 Hz, 2H), 2.64 (m, 2H), 2.36 (t, J=6.8 Hz, 2H), 2.50 (m, 3H), 1.90 (m, 3H), 1.70 (m, 2H). Anal. ($C_{24}H_{27}ClFNO_6$): C, H, N.

Measurements of the pharmacophoric distances for haloperidol and synthesized analogs may be conducted using SYBYL 6.8 (Tripos Associates, Inc., St Louis, Mo.). The X-ray crystal structure of haloperidol was used as the initial structure. The structures of synthetic compounds were built from SYBYL SKETCH with the chair conformation for pyrrolidine and an, axial hydroxyl group as starting geometry. This structure was minimized by the Powell method with 0.001 kcal/(mol Å) as the termination method. The minimized structure was then subjected to a systematic search for possible allowed conformations. The distance between the center of ring A and the nitrogen was constrained by the range allowed within the Humber (Humber et al, in *Computer Assisted Drug Design*; Olsen, E., Christoffersen, R., Eds.; ACS Symposium Series 112; American Chemical Society; Washington, D.C., 1979; pp 227-241 pharmacophore model), i.e., 4.9-6.9 Å. The conformation with the lowest energy from the search results is then used for measuring the distances.

Additional haloperidol analogs according to the invention are those having the formulae:

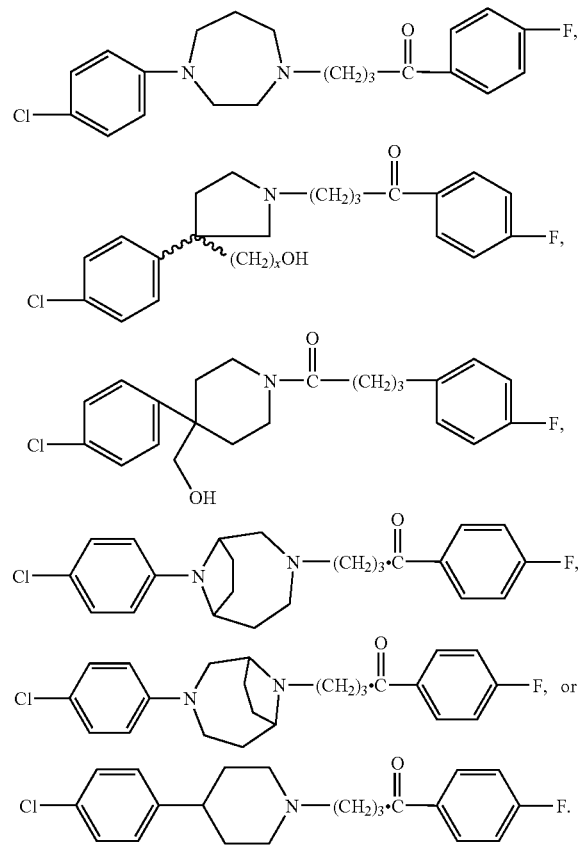

In addition to the specific analogs described above, those skilled in the art will appreciate that the invention also includes pharmaceutically acceptable salts, esters, derivatives, metal complexes, conjugates and prodrugs thereof of the conventional type that possess the same therapeutic profiles as the analogs themselves.

From the foregoing description, various modifications and changes in the composition and method will occur to those skilled in the art. All such modifications coming within the scope of the appended claims are intended to be included therein. The entire disclosures and contents of each and all references cited and discussed herein are expressly incorporated herein by reference. All percentages expressed herein are by weight unless otherwise indicated.

The invention claimed is:

1. A haloperidol analog having one of the formulae:

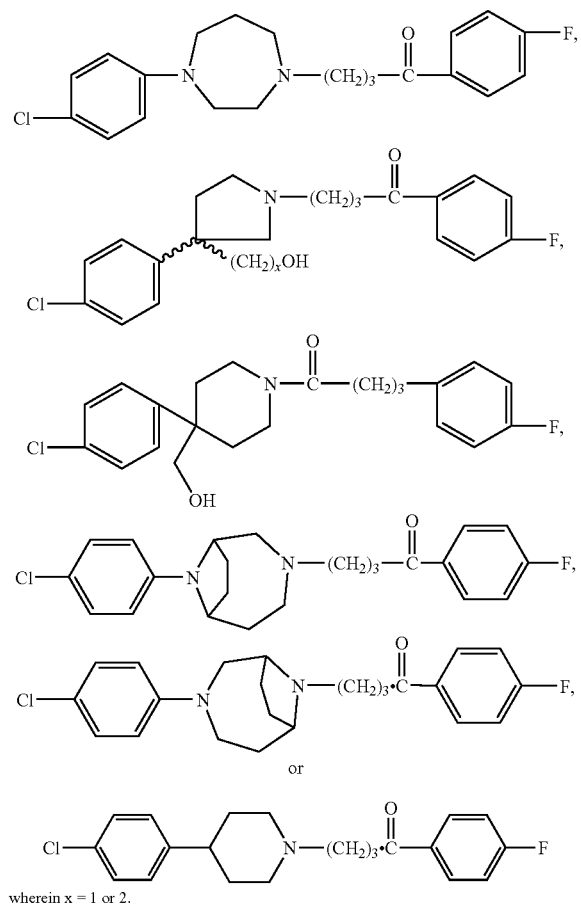

wherein x = 1 or 2.

2. A method for treating a mammalian patient suffering from psychosis comprising administration to the patient of a therapeutically effective amount of a haloperidol analog of claim 1.

3. A pharmaceutical composition comprising a haloperidol analog of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,700,587 B2 | Page 1 of 1 |
| APPLICATION NO. | : 10/934769 | |
| DATED | : April 20, 2010 | |
| INVENTOR(S) | : Seth Y. Ablordeppey and Donald M. N. Sikazwe | |

It is certified that error appears in the above-identified patent and that said Letters Patent is hereby corrected as shown below:

In the Specification

Column 1, line 3, please amend as follows:

This invention was made with government support under NIGMS MBRS # GM 08111, RCMI G12 RR 03020, and Title III grants awarded by the National Institutes of Health. The government has certain rights in the invention.

Signed and Sealed this
Twenty-seventh Day of October, 2015

Michelle K. Lee
*Director of the United States Patent and Trademark Office*